(12) United States Patent
Peckham et al.

(10) Patent No.: US 12,235,212 B1
(45) Date of Patent: Feb. 25, 2025

(54) PRECIOUS STONE TESTING APPARATUS AND METHOD THEREOF

(71) Applicant: Shenzhen Dikai Industrial Co., Ltd., Shenzhen (CN)

(72) Inventors: Gary Bruce Peckham, Shenzhen (GB); Xiuling Zhu, Shenzhen (CN)

(73) Assignee: Shenzhen Dikai Industrial Co., Ltd., Shenzhen (CN)

( * ) Notice: Subject to any disclaimer, the term of this patent is extended or adjusted under 35 U.S.C. 154(b) by 0 days.

(21) Appl. No.: 18/895,305

(22) Filed: Sep. 24, 2024

(30) Foreign Application Priority Data

Sep. 14, 2024 (CN) ......................... 202411293180.7

(51) Int. Cl.
*G01N 33/00* (2006.01)
*G01N 1/44* (2006.01)
*G01N 21/33* (2006.01)

(52) U.S. Cl.
CPC .............. *G01N 21/33* (2013.01); *G01N 1/44* (2013.01); *G01N 33/389* (2024.05); *G01N 2201/062* (2013.01)

(58) Field of Classification Search
CPC ........ G01N 21/33; G01N 1/44; G01N 33/389; G01N 2201/062
See application file for complete search history.

(56) References Cited

U.S. PATENT DOCUMENTS

| | | | |
|---|---|---|---|
| 5,835,205 A * | 11/1998 | Hunter | G01N 21/87 356/30 |
| 10,859,559 B1 * | 12/2020 | Tam | G02B 6/0005 |
| 2019/0137406 A1 * | 5/2019 | Zhu | G01N 27/02 |

* cited by examiner

*Primary Examiner* — Dani Fox
*Assistant Examiner* — Mamadou Faye
(74) *Attorney, Agent, or Firm* — David & Raymond Patent Firm; Raymond Y Chan

(57) ABSTRACT

A precious stone testing apparatus includes a testing circuit housed in a housing and tester probe unit extended from one end of the housing. The testing circuit includes a UVA/UVC LED module adapted to emit UVA LED light and UVC LED light onto a stone being tested and a heating system adapted to apply heat to the stone being tested. When the stone being tested is placed close to a testing end of a quartz light guide column, reflections of the UVA and UVC LED lights to the stone being tested are guided back to a UVA/UVC optical sensor while a thermal conductive tube encircling the quartz light guide column applies heat generated from the heating system to the surrounding of the stone being tested at the same time.

20 Claims, 9 Drawing Sheets

US 12,235,212 B1

PRECIOUS STONE TESTING APPARATUS AND METHOD THEREOF

CROSS REFERENCE OF RELATED APPLICATION

This application is a non-provisional application that claims the benefit of priority under 35U.S.C. § 119 to a Chinese application, application No. 2024112931807, filed Sep. 14, 2024, which is incorporated herewith by reference in its entirety.

BACKGROUND OF THE PRESENT INVENTION

Field of Invention

The present invention relates to a precious stone tester, and more particularly to a precious stone testing apparatus and method thereof for examining natural diamonds, cultivated diamonds (lad grown diamonds) made by high pressure high temperature method (HPHT) or chemical vapor deposition method (CVD), moissanite/ruby stones, gemstones, and other semi-gemstones or synthetic gemstones (cubic zirconia, glass or crystal) through detecting thermal conductivity and testing violet spectral absorption state.

Description of Related Arts

Colorless natural diamonds can absorb long-wave ultraviolet light (wavelength 365 nm) but not completely absorb short-wave ultraviolet light (short wavelength 265 nm), while CVD/HPHT/TYPE IIa diamonds can absorb both the long-wave and short-wave ultraviolet rays (256/365 nm). Colorless natural diamonds have the ability to transmit long-wave ultraviolet light (wavelength 365 nm) while the synthetic moissanite (moissanite) cannot completely absorb both the long-wave and short-wave ultraviolet lights. In addition, since the absorption of ultraviolet intensity for natural diamonds, moissanite and CVD/HPHT/TYPE IIa is different, for the same ultraviolet light source, the corresponding reflected ultraviolet light thereof is also different. Accordingly, according to this principle, the natural diamonds, moissanite and CVD/HPHT/TYPE IIa can be tested and distinguished.

CVD (Chemical Vapor Deposition) is a method used to create synthetic diamonds. In this process, a diamond seed crystal is placed in a chamber filled with carbon-rich gases, usually methane, that are then heated to a high temperature. The carbon atoms from the gas start to deposit on the diamond seed crystal, slowly forming a diamond crystal layer by layer. HPHT (High-Pressure High-Temperature) is a method used to create synthetic diamonds, and it can also be used to alter the color of natural diamonds. In this process, carbon is subjected to extremely high pressures and temperatures, mimicking the natural conditions under which diamonds form deep within the Earth's mantle. HPHT can be used to produce colorless diamonds or to change the color diamonds to make them more desirable for the market. TYPE IIa diamonds are a specific classification of diamonds that are almost or entirely devoid of nitrogen impurities, which are common in most diamonds. This makes Type IIa diamonds extremely pure and often very clear. They can occur naturally but are also commonly produced through synthetic methods like CVD or HPHT.

Besides, natural diamonds, HPHT/CVD, moissanite, rubies, sapphires, gemstones such as Zircon, synthetic gem-stones such as CZ (Cubic Zirconia), semi-precious stones, have different thermal conductivities. Therefore, by detecting the thermal conductivity of a precious stone, it is able to identify the precious stone. However, although natural diamond has the highest thermal conductivity in precious stones and can be quickly distinguished, CVD/HPHT, moissanite silicon carbide also has high thermal conductivity and thus it is not possible to distinguish CVD/HPHT, moissanite silicon carbide from natural diamond through the thermal conductivity tester.

Therefore, the dual detection mechanism using long-wave and short-wave ultraviolet (UV) lights as well as the thermal conductivity can distinguish between natural diamonds, HPHT/CVD, moissanite, rubies, sapphires, gemstones, CZ zircon, various semi-precious stones, and glass.

U.S. Pat. Nos. 8,947,111, 9,453,808, 11,073,483, and 11,243,170 disclose various multi-functional precious stone testing apparatuses and methods thereof, which comprise a LED light unit for providing an illumination at the conductive probe for determining thermal and/or electrical conductivity when the conductive probe contacts with the testing object without substantially transmitting heat from the LED light unit to the conductive probe as well as a UV light source and a sensor for determining various qualities of the testing object.

U.S. Pat. No. 7,595,628 discloses a probe for probing an electrical device under test. However, accurate probing is dependent on the operator's ability to visually locate the target node and the probe tip positions and ensure that the correct contact has been made between two. U.S. patent publication no. 2024/0027335 discloses a gemstone multi-tester instrument which includes a thermal conductive tube to be heated by a thermal testing assembly and an optical fiber coupled with an optical assembly for illuminating the stone under test with UV light and a tip for contacting the stone under test.

The long-wave and short-wave ultraviolet LED chips are conventionally packaged on a substrate that may be no adnormality in short period, but a period of use, the overall LED substrate chip will deteriorate, resulting in the spectra of the long-wave and short-wave are not in the correct range, affecting the accuracy of the tester. The user will not be informed of such deterioration and adnormality of the tester that may result economic and credit damages to both the user and the clients thereof.

SUMMARY OF THE PRESENT INVENTION

The invention is advantageous in that it provides a precious stone testing apparatus which is an all-in-one tester that can test all range of precious stones, including lab grown diamonds.

Another advantageous of the invention is to provide a precious stone testing apparatus and method thereof, wherein the precious stone testing apparatus allows the user to whether the stone being tested is gemstone, moissanite, natural diamond, or lab grown (CVD/HPHT/TYPE IIa) diamond at the same time by a single testing operation.

Another advantage of the invention is to provide a precious stone testing apparatus and method thereof, which long-wave UV lamp and short-wave UV lamp are configured independently to avoid deterioration and destruction of the UV lamps to ensure normal operation all the time.

Another advantage of the invention is to provide a precious stone testing apparatus and method thereof, which comprises a long-wave ultraviolet chip and a short-wave ultraviolet chip are packaged in the same plane, wherein a partition member is configured between the long-wave ultraviolet chip and the short-wave ultraviolet chip so as to block the short-wave UV light outside the substrate in such a manner that the packaging material structure of the long-wave ultraviolet chip is not affected and will not deteriorate even after a long period of operation time.

Additional advantages and features of the invention will become apparent from the description which follows and may be realized by means of the instrumentalities and combinations particular point out in the appended claims.

According to the present invention, the foregoing and other objects and advantages are attained by a precious stone testing apparatus, which comprises:
  a housing; and
  a testing circuit, housed in the housing, comprising:
    an optical system comprising at least one UVA/UVC optical sensor and a quartz light guide column having at least one portion extended out of the housing;
    a UVA/UVC LED unit, comprising a constant drive and at least one UVA/UVC module which comprises a substrate, a UVA LED chip, a UVC LED chip and a partition member, wherein the substrate is electrically connected to the constant drive via an electrical wiring, wherein the UVA LED chip and the UVC LED chip are arranged in a side by side manner to face the optical system so as to ensure a UVA LED light, in a wavelength range of 320 nm to 400 nm, emitted from the UVA LED chip and a UVC LED light, in a wavelength range of 200 nm to 280 nm, emitted from the UVC LED chip being directed and focused to a stone being tested, wherein the UVA LED chip and the UVC LED chip are arranged in a side by side manner for directing and focusing a UVA LED light emitted from the UVA LED chip and a UVC LED light emitted from the UVC LED chip to the stone being tested, and reflections of the UVA LED light and the UVC LED light penetrated through the stone being tested are guided and focused by the quartz light guide column to the UVA/UVC optical sensor, wherein the partition member is made of a UVC blocking material and arranged between the UVA LED chip and the UVC LED chip, such that the UVC LED light emitted from the UVC LED chip is blocked by the partition member from irradiating the UVA LED chip; and
    a central control unit, which is electrically connected with the UVA/UVC LED unit, the optical system, the heating system and the thermal conductive tube and configured to coordinate the UVA/UVA LED unit and the heating system for managing inputs, outputs and operations of the precious stone testing apparatus and providing test results.

In one embodiment, the testing circuit further comprises a heating system and a thermal conductive tube, wherein the thermal conductive tube, made of thermal conductive material, is configured to be heated by the heating system and has at least one portion extended out of the housing in such a manner that the quartz light guide column is arranged and extended in the thermal conductive tube coaxially to form a tester probe unit, so that by placing a testing end of the thermal conductive tube on the stone being tested for applying heat generated from the heating system to the stone being tested, the quartz light guide column is positioned close to the stone being tested simultaneously to receive reflections of the UVA LED light and the UVC LED light after penetrating through the stone being tested.

In one embodiment, the UVA/UVC optical sensor of the optical system further is configured to monitor light intensity and detect the reflections of the UVA LED light and the UVC LED light. The optical system further comprises one or more operational amplifiers configured to be used in the UVA/UVC optical sensor for signal amplification and conditioning. The UVA LED light emitted from the UVA LED lamp and the UVC LED light emitted from the UVC LED lamp are directed and focused onto the stone being tested through the quartz light guide column. Then, the quartz light guide column receives and guides reflections of the UV light back from the stone being tested to a UVA/UVC optical sensor for detection. At the same time, the thermal conductive tube, encircling said quartz light guide column, applies heat generated from the heating system to the stone being tested.

In one embodiment, the substrate has a UVA socket and a UVC socket which are indented in an emitting side thereof and configured to face the optical system, wherein the UVA LED chip is arranged in the UVA socket to form a UVA LED lamp and the UVC LED chip is arranged in the UVC socket to form a UVC LED lamp.

In one embodiment, the partition member is a partition wall isolating the UVA socket and the UVC socket in the emitting side of the substrate.

In one embodiment, the UVA LED chip is arranged close to one side of the partition member and the UVC LED chip is arranged close to another side of the partition member.

In one embodiment, the UVC LED chip is larger than the UVA LED chip and the UVC socket is larger than the UVA socket in size.

In one embodiment, the heating system comprises a heating device and a heating drive, connected with the central control unit, wherein the heating device is configured to heat the thermal conductive tube and controlled by the central control unit through the heating drive.

In one embodiment, the heating device is embodied as a PTC (positive temperature coefficient) heating device.

In one embodiment, the testing circuit further comprises a metallic detection device connected with the central control unit and configured to identify a presence of metallic material contained in the stone being tested to determine whether the stone being tested containing metal material such as gemstones, synthetic gemstones such as CZ zircon and mega thermal stones.

In accordance with another aspect of the invention, the present invention provides a precious stone testing method of a precious stone testing apparatus, comprising steps of:
  (a) initializing the precious stone testing apparatus;
  (b) determining whether devices of the precious stone testing apparatus being heated to a set temperature, if yes, the precious stone testing apparatus entering a standby mode, accepting commands and ready for testing, if no, continuing to heat the devices of the precious stone testing apparatus,
  (c) conducting a metal test by a metallic detection device to determine whether the precious stone being tested containing metal material, such as the setting around the perimeter of the stone being tested,
    if yes, displaying metal test result through a display device and/or providing audio alarm for a predetermined period of time through an audio device, if no, go to the next step (d);
  (d) conducting a thermal conductivity test by a heating system to determine whether the stone being tested is gemstone, synthetic gemstone such as CZ zircon,
    if yes, displaying gemstone, synthetic gemstone such as cubic zirconia (CZ zircon) test result through the display device and/or providing audio alarm through the audio device, if no, go to the next step (e);

(e) starting a UVA LED lamp and a UVC LED lamp and conducting a UVA test and a UVC test correspondingly to the stone being tested to determine whether the stone being tested is natural diamond, moissanite or CVD/HPHT/TYPE IIa; and (f) analyzing tested data obtained in the UVA test and the UVC test to determine whether the stone being tested is natural diamond, moissanite or CVD/HPHT/TYPE IIa and displaying the natural diamond, moissanite or CVD/HPHT/TYPE IIa test result through the display device and/or providing audio broadcast through the audio device.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1A:
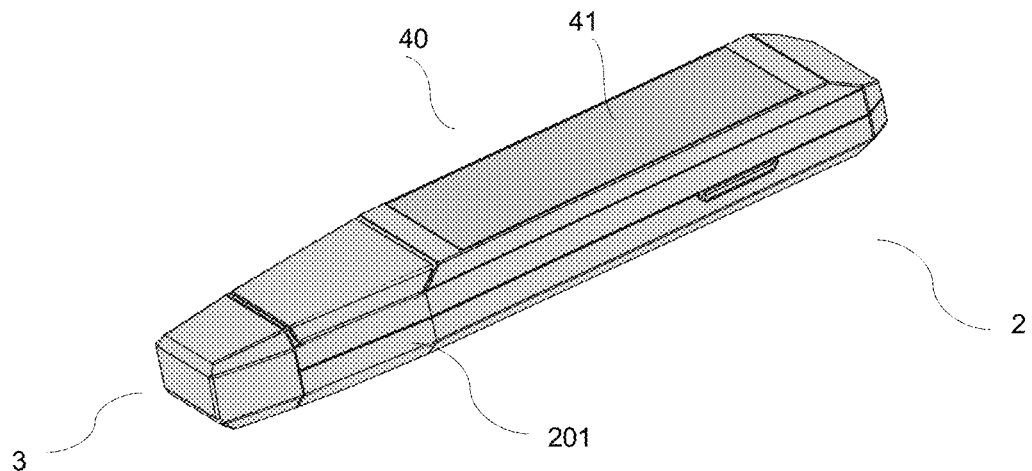
FIG. 1A is a front perspective view of a precious stone testing apparatus according to a preferred embodiment of the present invention.
Figure 1B:
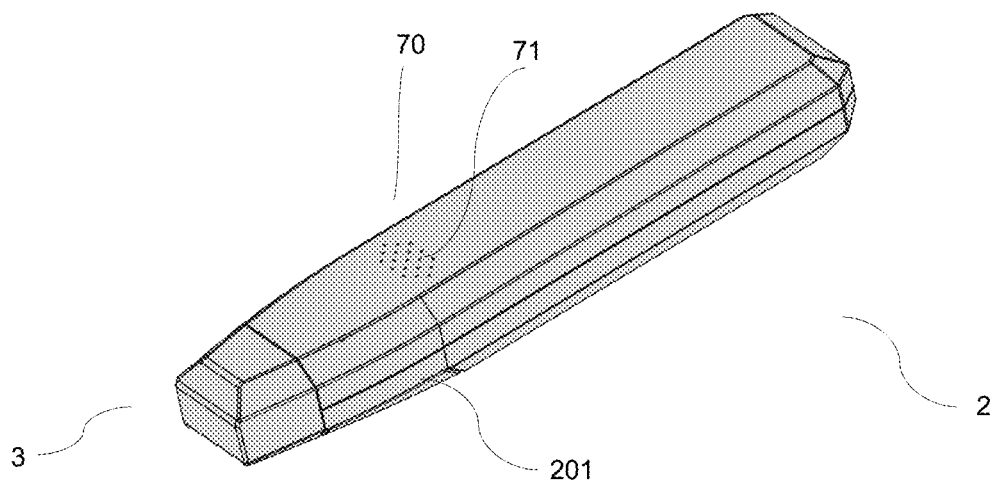
FIG. 1B is a rear perspective view of the precious stone testing apparatus according to the above preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

In the description of the present invention, unless explicitly stated otherwise and qualified, terms such as "connected," "attached," and "fixed" should be construed broadly. For instance, these terms may indicate a permanent connection or a detachable one, or they may refer to a whole unit. They can signify a mechanical linkage, an electrical connection, direct coupling, or indirect interaction through an intermediary medium. Whether these terms imply an internal connection between two elements or an interactive relationship between them will depend on the specific context and the understanding of those skilled in the art.

Throughout this invention, unless explicitly stated otherwise and qualified, when the first feature is described as being "above" or "below" the second feature, this may entail direct physical contact between the two features. Alternatively, it may signify that the first and second features are not in direct contact but are linked through the involvement of additional features. Additionally, the description of the first feature being "above," "over," or "on top of" the second feature includes scenarios where the first feature is positioned directly above or diagonally above the second feature or simply means that the first feature is situated at a higher horizontal level than the second feature. Conversely, when the first feature is referred to as "below," "under," or "beneath" the second feature, it encompasses cases where the first feature is directly below or diagonally below the second feature or simply implies that the first feature's horizontal height is less than that of the second feature.

In this embodiment's description, terms such as "up," "down," "right," and "left" are used to describe orientations or positional relationships. These descriptions are based on the orientations or positions depicted in the drawings and are employed for ease of explanation and simplification of operation. They should not be construed as indications or implications that the device or element being discussed must possess a specific orientation, be constructed in a particular manner, or operate exclusively in a certain orientation. Furthermore, terms such as "first" and "second" are employed solely for the purpose of distinction in the description and do not carry any particular significance.

Figure 2:
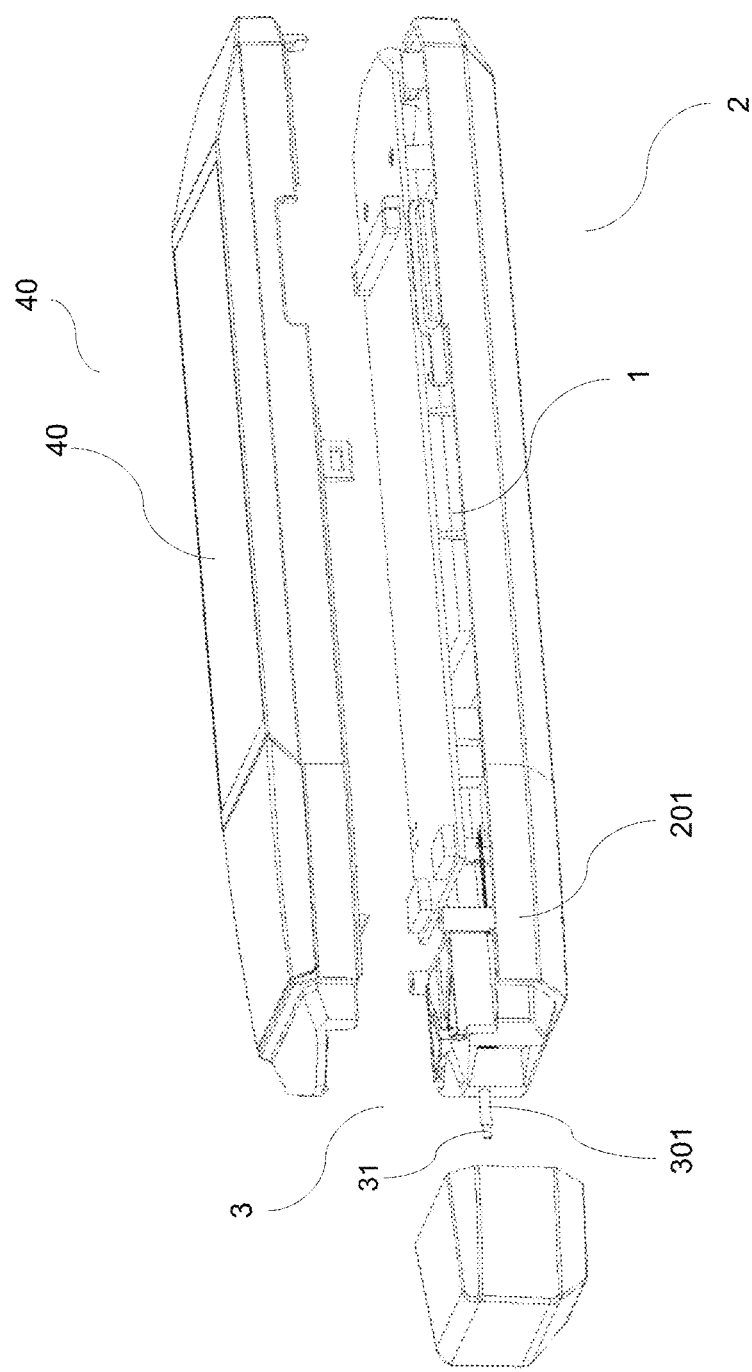
FIG. 2 is an exploded view of the precious stone testing apparatus according to the above preferred embodiment of the present invention.
Figure 3A:
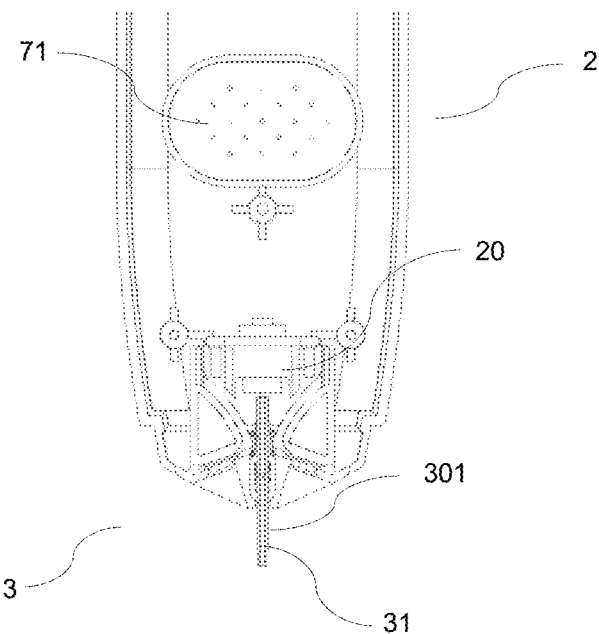
FIG. 3A is a partial sectional view of a front portion of the precious stone testing apparatus according to the above preferred embodiment of the present invention.
Figure 3B:
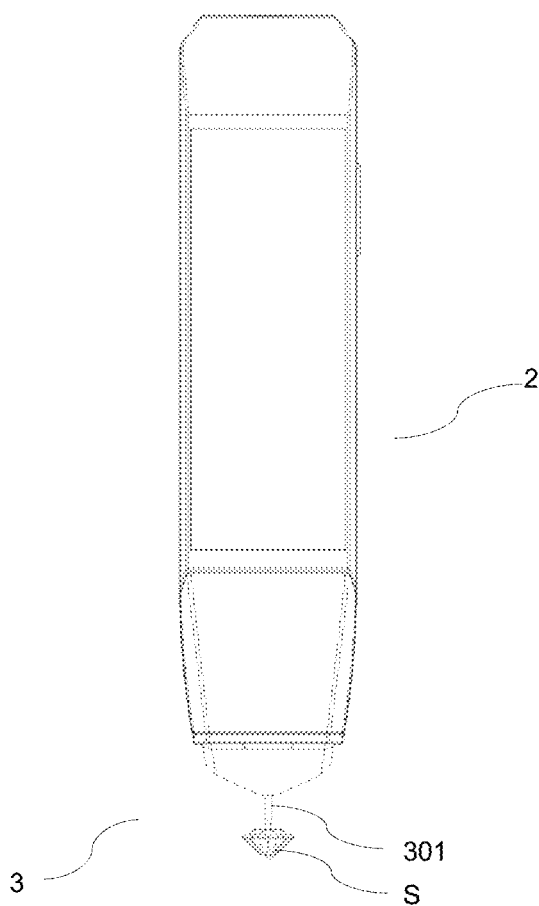
FIG. 3B is a schematic view illustrating the test probe unit of the precious stone testing apparatus pressing against a stone being tested according to the above preferred embodiment of the present invention.
Figure 4A:
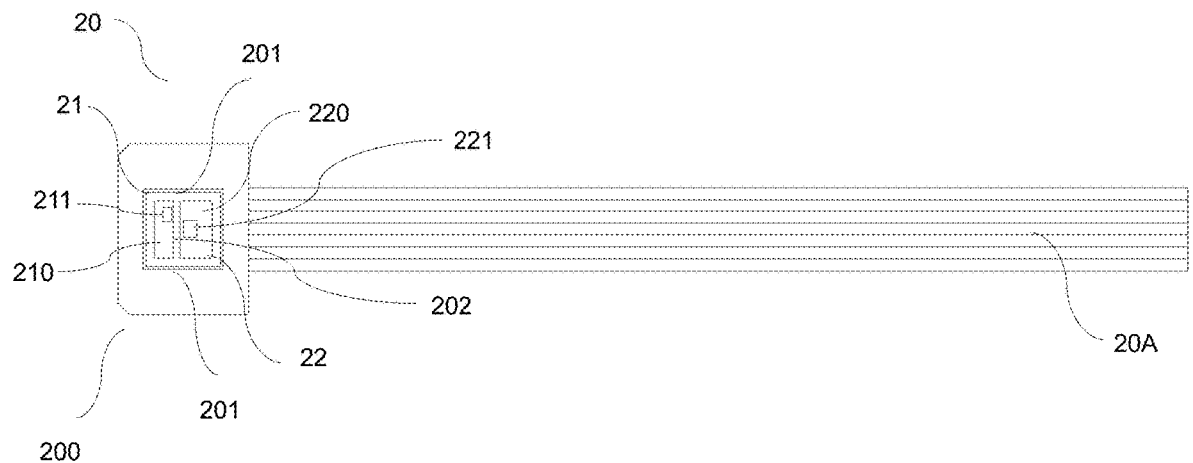
FIG. 4A is an elevation view illustrating the UVA/UVC module of the precious stone testing apparatus according to the above preferred embodiment of the present invention.
Figure 4B:
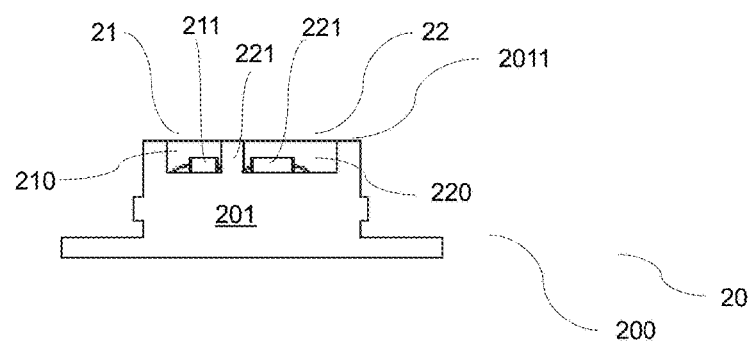
FIG. 4B is a sectional view illustrating the UVA/UVC module of the precious stone testing apparatus according to the above preferred embodiment of the present invention.
Figure 5:
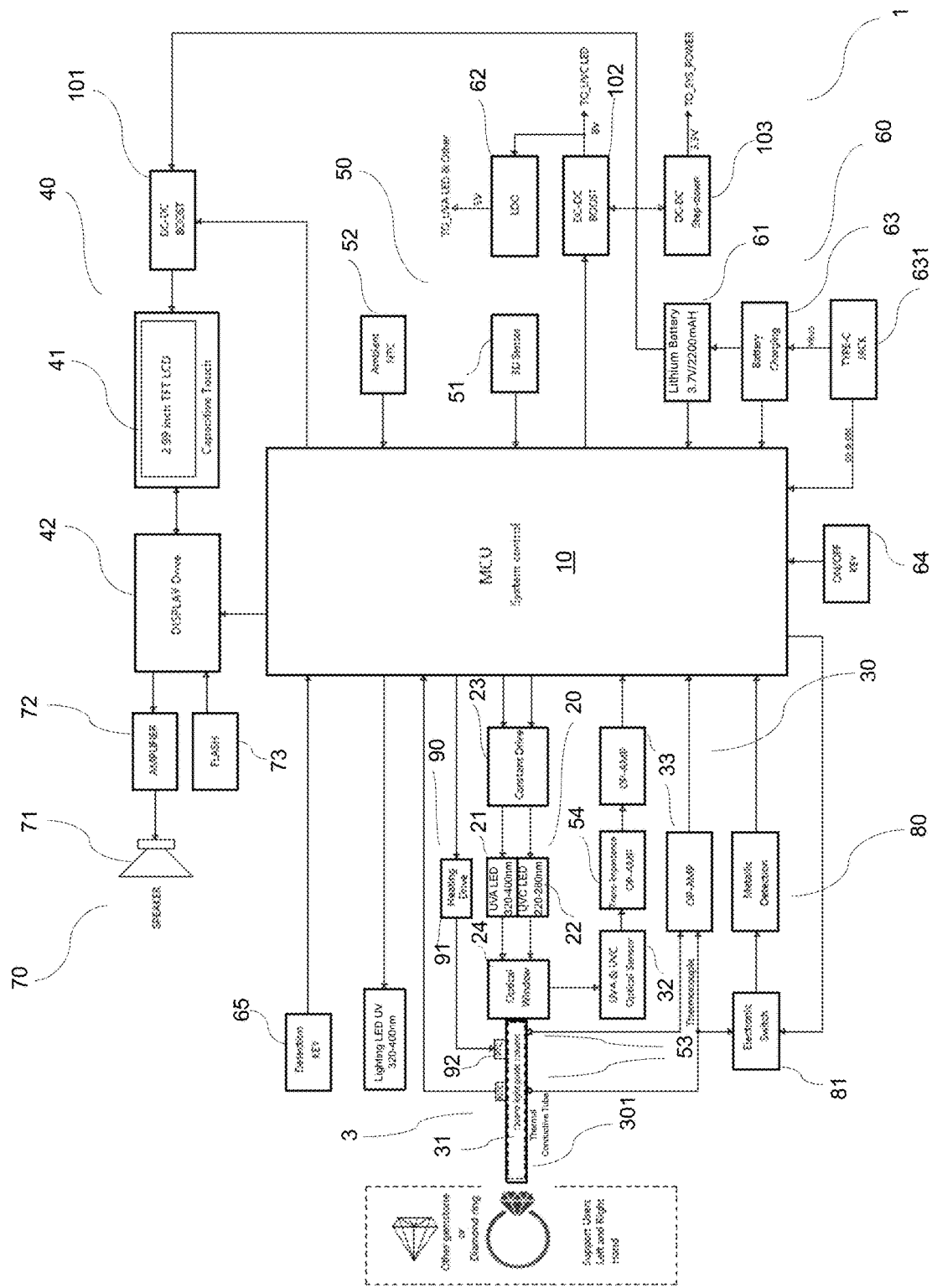
FIG. 5 is a circuit diagram of the precious stone testing apparatus according to the above preferred embodiment of the present invention.

Referring to FIG. 1A to FIG. 9, a precious stone testing apparatus and method thereof according to a preferred embodiment of the present invention is illustrated, wherein the precious stone testing apparatus comprises a testing circuit 1, a housing 2 housing the testing circuit 1 therein and a tester probe unit 3 which is electrically connected to the testing circuit 1 and comprises a thermal conductive tube 301, made of thermal conductive material such as metal like copper, having at least one portion extended out of the housing 2, as show in FIG. 2, FIG. 3A and FIG. 5. The testing circuit 1 comprises a central control unit 10, a UVA/UVC LED unit 20, an optical system 30, a display device 40, a detection device 50, a power supply and management system 60, an audio device 70, a metallic detection device 80, and a heating system 90.

Referring to FIG. 5, the central control unit 10 is embodied as a microcontroller unit (MCU) is configured to coordinate the UVA/UVC LED unit 20, the optical system 30, the thermal conductive tube 301, the display device 40, the detection device 50, the power supply and management system 60, the audio device 70, the metallic detection device 80, and the heating system 90 for managing inputs, outputs and overall operations of the precious stone testing apparatus and providing test results.

Referring to FIG. 3A to FIG. 5, the UVA/UVC LED unit 20, connected to the central control unit 10, comprises at least one UVA/UVC module 200 which comprises a UVA (Ultraviolet A) LED (Light Emitting Diode) lamp 21 configured to emit a type of ultraviolet A radiation (long-wave ultraviolet (UV) light) in a wavelength range of 320 nm to 400 nm, preferably 365 nm, for processing required UVA exposure, a UVC (Ultraviolet C) LED lamp 22 configured to emit a type of ultraviolet C radiation (short-wave ultraviolet (UV) light) at a wavelength range of 200 nm to 280 nm, preferably 265 nm, for processing required UVC exposure, a constant drive 23, and an optical window 24.

Figure 3C:
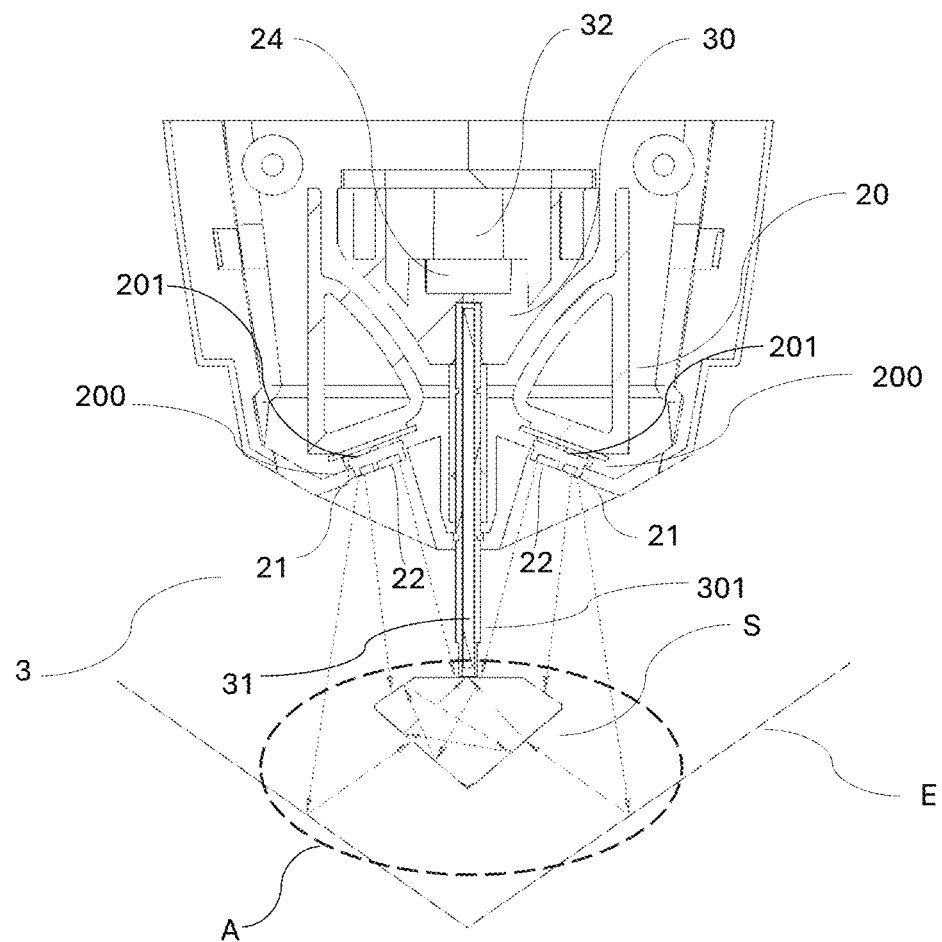
FIG. 3C is a partial sectional view of the precious stone testing apparatus with the test probe unit thereof contacting with a surface of the stone being tested according to the above preferred embodiment of the present invention.

According to the preferred embodiment of the present invention, referring to FIG. 3C, the UVA/UVC unit 20 is embodied to comprise two UVA/UVC modules 200 connecting to the constant drive 23 and the central control unit 10 via an electrical wiring 20A, wherein the two UVA/UVC modules 200 are mounted inclinedly at two opposing sides of the quartz light guide column 31 such that the UVA LED lights and the UVC LED lights emitted from the two UVA/UVC modules 200 are directed to a target area A.

Referring to FIG. 4A and FIG. 4B, each of the UVA/UVC modules 200 comprises a substrate 201, a long-wave ultraviolet chip, embodied as a UVA LED chip 211, and a short-wave ultraviolet chip, embodied as a UVC LED chip 221. The substrate 201 has UVA socket 210 and a UVC socket 220 indented in an emitting side 2011 configured to face the optical system 30. The UVA LED chip 211 is arranged in the UVA socket 210 to form the UVA LED lamp 21 and the UVC LED chip 221 is arranged in the UVC socket 220 to form the UVC LED lamp 22 side by side on the substrate 201.

The optical system 30, connected to the central control unit 10, comprises a quartz light guide column 31 which is arranged adjacent to the at least one UVA/UVC module 200. As shown in FIG. 3C, according to the preferred embodiment, the quartz light guide column 31 is coaxially between the two UVA/UVC modules 200 while a testing end of the quartz light guide column 31 is extended to the target area A where the UVA LED lights and the UVC LED lights emitted from the UVA LED chips 211 and the UVC LED chips 221 of the two UVA/UVC modules 200 are directed thereto, such that when the testing end of the quartz light guide column 31 is in contact with a surface of the stone to be tested S, the UVA LED lights and the UVC LED lights are directed and illuminate on the stone to be tested S.

In particular, the UVA LED chip 211 in the UVA socket 210 and the UVC LED chip 221 in the UVC socket 220 and configured to direct and focus the long-wave and short-wave UV lights from the UVA LED lamp 21 and the UVC LED lamp 22 onto the target area A so as to ensure precise delivery of both the long-wave UVA LED light (ranged 320 nm-400 nm) and the short-wave UVC LED light (ranged 200 nm-280 nm) to the stone to be tested S.

The optical system 30 further comprises a UVA/UVC optical sensor 32 configured to monitor light intensity and detect reflections of the UVA LED light and the UVC LED light after penetrating through the stone being tested S, operational amplifiers (OP-AMP) 33 configured to be used in the UVA/UVC optical sensor 32 for signal amplification and conditioning.

The quartz light guide column 31 is arranged in the thermal conductive tube 301 coaxially to collect and guide the reflections of the long-wave and short wave UV lights (UVA LED lights and UVC LED lights) which have penetrated through the stone being tested S back to the UVA/UVC optical sensor 32. Since the quartz is an excellent material for the purpose of light collection due to its high transparency and low absorption in the ultraviolet range. During testing operation, after the UVA LED light and the UVC LED light emitted from the UVA LED lamp 21 and the USC LED lamp 22 strike and illuminate the precious stone being tested S, the reflections of the UVA LED light and the UVC LED light back from the precious stone being tested S are directed, guided and focused by the quartz light guide column 31 to the UVA/UVC optical sensor 32 via the optical window 24.

The optical window 24 is arranged for filtering specific wavelengths of the UV light to allow only desired wavelengths (UVA/USC) to pass through while blocking unwanted wavelengths or environmental interference and the UVA/UVC optical sensor 32 is arranged behind the optical window 24 so as to protect the UVA/UVC optical sensor 32 from environmental factors like dust, moisture or physical damage, ensuring consistent performance and preventing contamination, so that the accuracy of readings and measurements form the UVA/UVC optical sensor 32 can be ensured.

In order to direct and focus the long-wave and short-wave UV lights from the UVA LED chip 211 and the UVC LED chip 221 onto the target area A, the UVA LED chip 211 and the UVC LED chip 221 are preferred to be arranged side by side adjacent to the quartz light guide column 31. It is appreciated that the configuration of the UVA socket 210 and the UVC socket 220 in the substrate 201 of the UVA/UVC module 200 side by side forms a partition member 202 between the UVA LED chip 211 and the UVC LED chip 221. The partition member 202 is preferred to be made of a UVC blocking material that can effectively block the strong penetrative UVC radiation with a wavelength between 200-280 nanometers, such as glass, acrylic, polycarbonate, metals (like aluminum or steel), or material coated with a UVC-blocking film or coating, so as to block the short-wave ultraviolet light emitted from the UVC LED chip 221 of the UVC LED lamp 22 irradiating to the UVA LED lamp 21 and the UVA LED chip 211 thereof.

According to the preferred embodiment, the partition member 202 is embodied as an isolation wall formed between the UVA socket 210 and the UVC socket 220 and extended from bottoms to top openings of the UVA socket 210 and the UVC socket 220, so that the UVA socket 210 and the UC socket 220 are arranged side by side and the partition member 202 isolates the UVA LED chip 211 from the UVC LED chip 221, or alternatively, the partition member 202 isolates the UVC LED chip 221 from the UVA LED chip 211, so as to block the short-wave UV light outside the substrate such that the packaging material structure of the long-wave UVA LED chip 211 is not affected and will not deteriorate even after a long period of operation/ irradiation time, that greatly ensures the testing precision of the precious stone testing apparatus of the present invention.

According to the preferred embodiment, as shown in FIG. 4A and FIG. 4B, the presence of the partition member 202 allows the UVA LED chip 211 being installed in the UVA socket 210 of the substrate 201 as close as possible to one side of the partition member 202 and the UVC LED chip 221 being installed in the UVC socket 220 of the substrate 201 as close as possible to another side of the partition member 202, so that a distance between the UVA LED chip 211 of the UVA LED lamp 21 and the UVC LED chip 221 of the UVC LED lamp 22 may merely as close as a thickness the partition member 202, that further facilitates the direct and focus of both the UVA LED light emitted from the UVA LED chip 211 and the UVC LED light emitted from the UVC LED chip 221 to the target through the quartz light guide column 31.

Further, the substrate 201 can be made of the UVC blocking material, so that the partition wall between the UVA socket 210 and the UVC socket 220 forms the partition member 202.

In addition, the UVC socket 220 is preferred to be larger than the UVA socket 210 in size for die attaching a larger UVC LED chip 221 since the UVC LED chip 221 typically requires more power to generate the same amount of light as the UVA LED chip 211 because the UVC LED light is more energetic and harder to produce efficiently. In addition, a larger chip size of the UVC LED chip 221 and a larger size of the UVC socket 220 significantly help dissipate heat more effectively while the UVC LED chip 221 generates more heat than the UVA LED chip 211 due to their higher energy requirements and less efficient light production. In other words, the larger UVC LED chip 221 can accommodate the higher power requirements, and the larger UVC socket 220 not only provides more space for electrical connections and handling higher currents that the UVC LED chip 221 requires, but also allows for better thermal management, helping to dissipate heat more effectively and preventing damage to the UVC LED chip 221, and withstands operational stresses.

Since the long-wave UV lamp (UVA LED lamp) 21 and the short-wave UV lamp (UVC LED lamp) 22 are configured independently by die bonding in the UVA socket 210 and the UVC socket 220 respectively of the substrate 201, deterioration and destruction of the UVA LED lamp 21 and the UVC LED lamp 22 can be avoided to ensure normal operation at all time.

It is appreciated that, when the testing end of the quartz light guide column 31 is close to the stone being tested S by pressing a free end of the thermal conductive tube 301 against a surface of the stone being tested S, as shown in FIG. 3C, the UVA LED lights and the UVC LED lights emitted from the two UVA/UVC modules 200 illuminate and penetrate through the stone being tested S. The UVA LED lights and the UVC LED lights are reflected in the stone being tested S forming the reflections, wherein the reflections of the UVA LED lights and the UVC LED lights concentrated at the position of the quartz light guide column 31 are collected and guided to enter UVA/UVC optical sensor 32 through the quartz light guide column 31. When a shelter element E is used behind the stone being tested S, portions of the UVA LED lights and the UVC LED lights hit the shelter element E near the stone being tested S and then penetrate the stone being tested S will also be collected and guided by the quartz light guide column 31 to the UVA/UVC optical sensor 32 for detecting and testing.

As mentioned above, colorless natural diamonds can absorb long-wave UV light (wavelength 365 nm) but cannot fully absorb short-wave UV light (wavelength 265 nm). In contrast, CVD/HPHT/IIa diamonds can absorb both long-wave and short-wave UV lights (256 nm/365 nm). Colorless natural diamonds transmit long-wave UV light (wavelength 365 nm), while synthetic moissanite does not fully absorb long-wave and short-wave UV lights. In addition, due to the different UV absorption intensity of natural diamonds, moissanite and CVD/HPHT/IIa diamonds, the corresponding reflections of long-wave and short-wave UV lights will be different for the same UV light source (UVA/UVC module 200). Therefore, based on this principle, natural diamonds, moissanite and CVD/HPHT/IIa diamonds can be tested and distinguished. Also, the two wavelengths of the long-wave and short-wave UV lights have different absorption or transmittance for each type of stone, and the stone can be distinguished by the analysis of the reflections of the UVA LED light and the UVC LED light after penetrating through the stone being tested S are refracted back to the quartz light guide column 31.

Referring to FIG. 5, the display device 40, connected to the central control unit 10, comprises a display screen 41 which is embodied as a TFT LCD, such as 2.9-inch TFE LCD capacitive touch screen, for displaying test results provided by the central control unit 10 as well as other information such as system status, current status, settings, alerts, notifications, and user information, and a display drive 42 adapted to manage the display output. Users are able to interact with the precious stone testing apparatus via the display screen 41 for adjusting settings and initiating testing processes.

The detection device 50, connected with the central control unit 10, comprises a 3D sensor 51 connected to the central control unit 10 and configured to detect the position and movement of the precious stone testing apparatus for alignment and monitoring purposes, an ambient NTC (Negative Temperature Coefficient) sensor 52 connected to the central control unit 10 and configured to measure temperature, monitoring and control, one or more thermocouples 53, and a trans-impedance OP-AMP 54 configured to convert current from the 3D sensor 51 and thermocouple and NTC sensor 52 into a voltage signal.

The power supply and management system 60 comprises a power source 61, embodied as a rechargeable Lithium Battery (3.7V/2200 mAh) for powering the precious stone testing apparatus, a low dropout regulator (LDO) 62 configured to provide stable voltage supply to the UVA LED lamps 21 and the UVC LED lamps 22, a battery charging unit 63 with a type-C charging jack 631 configured for charging the power source 61, a switch key 64, embodied as an ON/OFF key, for switching on/off of the power source 61 of the precious stone testing apparatus, and a detection key 65 configured to allow a user interaction with the precious stone testing apparatus for specific commands.

The audio device 70, connected with the central control unit 10 and configured to deliver audio alerts and/or notifications, comprises one or more speakers 71 provided for audio feedback, information and alerts to the user, an amplifier 72 configured to enhance audio signal strength for clear sound output, and at least a flash memory 73 configured to store audio and display data and system configurations.

The metallic detection device 80 is connected with the central control unit 10 and configured to identify the presence of metallic materials and comprises an electronic switch 81 configured to manage power distribution and/or signal routing.

The heating system 90 comprises a heating drive 91 and a heating device 92 connected with the central control unit 10, wherein said heating device 92 is configured to heat the thermal conductive tube 301 of the tester probe unit 3 and controlled by the central control unit 10 through a heating drive 91.

The central control unit 10 is configured to manage operations, process inputs from the detection device 50 and the metallic detection device 80, and control outputs the UVA/UVC LED unit 20 and the heating system.

The emitting of the long-wave (365 nm) UV light from the UVA LED lamp 21 and the short-wave (265 nm) UV light from the UVC LED lamp 22 is controlled by the constant drive 23 to interact with the stone to be tested S. The heating system 90 is controlled by the heating drive 91 for stable operation.

As mentioned above, the quartz light guide column 31 is arranged to precisely guide and focus the reflections of both the long-wave (365 nm) UV light and the short-wave (265 nm) UV light that have penetrated through the stone to be tested S back to the optical sensor 32 via the optical window 24. The UVA/UVC optical sensor 32 is configured to monitor the intensity and characteristics of the light interacting with the stone to be tested S. The operational amplifiers (OP-AMPs) 33 are configured for amplifying detected signals for processing by the central control unit 10.

The 3D sensor 51 is configured to detect positional and movement data so as to ensure proper alignment of the stone to be tested S with the quartz light guide column 31 and the thermal conductive tube 301 of the tester probe unit 3. The ambient NTC sensor 52 is configured to measure an ambient temperature to adjust the operation of the precious stone testing apparatus accordingly. The one or more thermocouples 53 are extended to the thermal conductive tube 301 and configured to measure the temperature around the stone to be tested S, while one of the operational amplifiers 33 amplifies the detected thermal signals from the one or more thermocouples 53 to the central control unit 10.

The display screen 41 of the display device 40 provides a user interface for monitoring and controlling the precious stone testing apparatus.

In order to regulate voltage levels for different components, such as 3.3 V, 5V and 8V, the precious stone testing apparatus may further comprise one or more converters, including a DC-DC boost converter 101 for the display device 40, a DC-DC boost converter 102 and a DC-DC Step-down Converter 103 for the low dropout regulator 62 so as to ensure all components of the precious stone testing apparatus receive appropriate power levels.

When the precious stone testing apparatus is activated via the ON/OFF key 64, the central control unit 10 is initiated to first perform initial checks on the UVA/UVC LED unit 20, the optical system 30, a display device 40, the detection device 50, the power supply and management system 60, the audio device 70, the metallic detection device 80, and the heating system 90.

During the testing process, the UVA/UVC optical sensor 32 and the thermocouple 53 continuously send feedback to the central control unit 10 and the central control unit 10 adjusts the intensities of the long-wave UVA LED lights and the short-wave UVC LED light as well as the heating of the heating system 90 to maintain optimal testing conditions, such as using PWM and constant current techniques.

By emitting and directing the long-wave UV light from the UVA LED lamp 21 and the short-wave UV light from the UVC LED lamp 22 to the specific target area A where the stone to be tested S is positioned, the long-wave and short-wave UV lights interact with the stone to be tested S and the optical system 30 and the detection device 50 monitor the responses to determine the properties or authenticity of the stone to be tested S after the central control unit 10 processes the detected data to evaluate the precious stone being test such as using pre-stored algorithms and reference data. Of course, upon the testing operation completion, the precious stone testing apparatus can power down or enter standby mode, ready for further commands.

In view of above, the precious stone testing apparatus is designed for precise evaluation of precious stone using long-wave UVA LED light and short-wave UVC LED light, thermal management, and sensing technologies. The central control unit 10 coordinates the integration of the optical system 30 and detection device 50 and controls allows for dynamic adjustments, making the precious stone testing apparatus suitable for applications requiring meticulous environmental management and user feedback.

Figure 6:
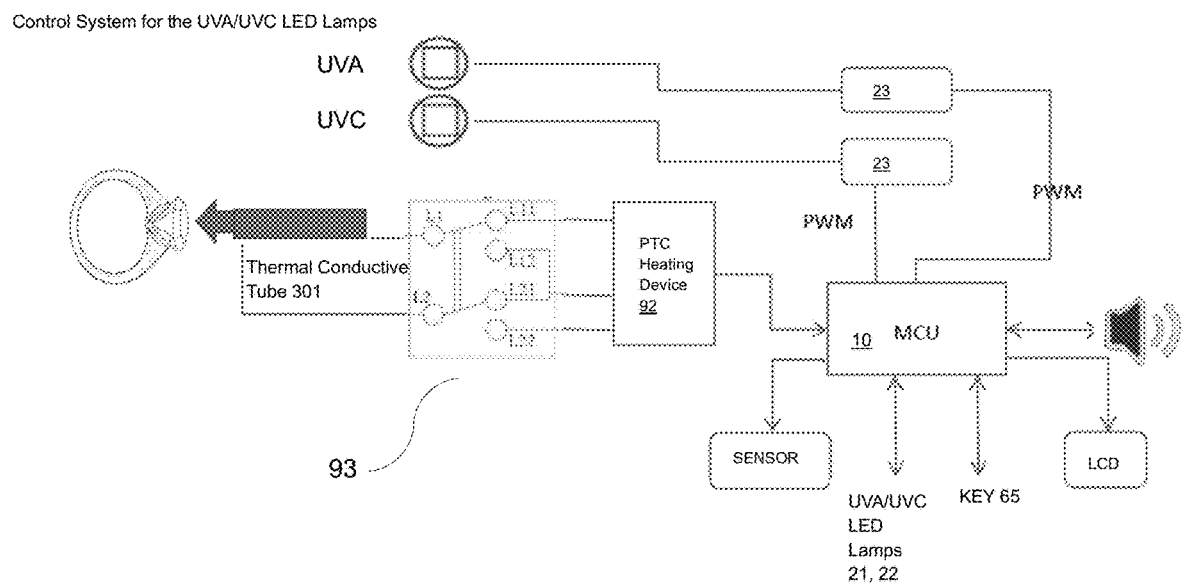
FIG. 6 is a block diagram illustrating a control system for the UVA/UVC LED lamps of the precious stone testing apparatus according to the above preferred embodiment of the present invention.

Referring to FIG. 6, a control system for the UVA and UVC LED lamps 21, 22 is illustrated, which integrates the long-wave and short wave UV light emission and heating control with user interaction, offering a versatile solution for applications requiring precise UV treatment and temperature management while the central control unit 10 orchestrates the operation, ensuring stability and safety through dynamic feedback and control.

The intensity of the UVA LED lamp 21 and the intensity of the UVC LED lamp 22 are controlled by the constant drive 23 to ensure stable current operation so as to ensure consistent light output and prevent damage from current fluctuations while pulse width modulation (PWM) signals from the central control unit 10 are used to adjust the intensities of the UVA/UVC LED lamps 21, 22 and the UV lights output according to the requirements of the precious stone testing apparatus.

The heating device 92 of the heating system 30 is embodied as a positive temperature coefficient (PTC) heating device which is a type of electric heating device utilizing PTC thermistors as the heating element, wherein the PTC thermistors are generally ceramic materials that their electrical resistance increases significantly as their temperature rises. The PTC heating system 90 provides heating to the thermal conductive tube 301, wherein the heat output required is also controlled by PWM signals from the central control unit 10.

The thermal conductive tube 301 serves as a conduit for the UV lights and heat, directing the heat towards a specific target area of the stone to be tested S. The sensors refer to UVA/UVC optical sensor 32 of the optical system and the 3D sensor 51, the ambient NTC sensor 52 and thermocouple 53 of the detection device 50, which monitor parameters of temperature, light intensity and other environmental conditions and provide feedback to the central control unit 10.

A relay device 93 is arranged between the PTC heating device 92 and the thermal conductive tube 301, providing electrically operated switches via contacts or connections L1, L2, L11, L12, L21, and L22 for controlling the flow of electrical current in this circuit.

The connections L1 and L2 are main power input lines to a relay coil of the relay device 93, wherein when the relay device 93 is energized by applying voltage across L1 and L2, it closes the contacts between the corresponding pairs of connections (L11, L12, L21, L22), allowing current to pass through those connections. The central control unit 10 controls the voltage to the coil, thus controlling whether the relay device 93 is engaged (contacts closed) or disengaged (contacts open). The connections L11 and L12 are a pair of contacts within the relay device 93, wherein when the relay device 93 is energized, the connection L11 and L12 would close, allowing current to flow between these two points. Such connection is arranged to control the power supply to the PTC heating device 92, turning it on or off depending on whether the relay device 93 is engaged. In addition, the connections L11 and L12 are connected to the thermal conductive tube 301, acting as a sensor to provide feedback to the central control unit 10 regarding temperature.

The connections L21 and L22 are another pair of contacts within the relay device 93, wherein when the relay device 93 is energized, the connections L21 and L22 would close, allowing current to flow between these two points. Such connection is used to control another part of the power to the central control unit 10 and the heating element in the PTC heating device 92. Also, the connections L21 and L22 are also linked to the thermal conductive tube 301 so as for controlling the operation of the circuit based on the temperature feedback from the thermal conductive tube 301.

The thermal conductive tube 301 is also configured as a temperature sensor that monitors a temperature of the thermal conductive tube 301 while keeping the temperature within a set range at all times and sends the detected data to the central control unit 10. The PTC heating device 92 is configured to heat the stone to be tested S via the thermal conductive tube 301 to a specific temperature required for testing, wherein the heating process is controlled by the relay device 93.

The central control unit 10 processes the temperature data from the thermal conductive tube 301 and determines whether to energize the connections L1, L2 of the relay device 93. If the temperature is below a predetermined threshold, the central control unit 10 might energize the relay device 93, closing the contacts between connections L11 and L12 (and possibly connections L21 and L22), thereby powering the PTC heating device. If the temperature reaches the predetermined threshold, the central control unit 10 might de-energize the relay device 93, opening the contacts, which cuts off the power to the PTC heating device 92, preventing further heating.

Figure 7:
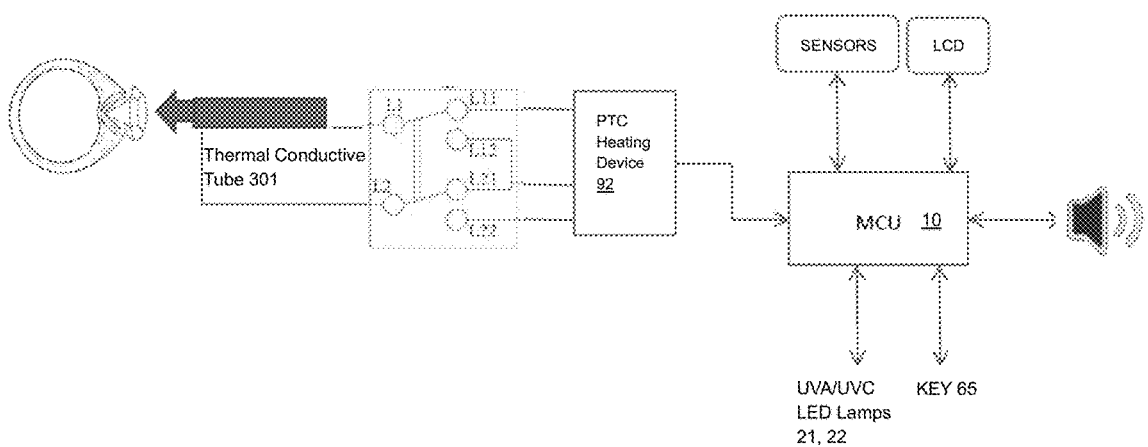
FIG. 7 is a block diagram illustrating a heating system of the precious stone testing apparatus according to the above preferred embodiment of the present invention.

FIG. 7 illustrates a block diagram of the heating system 90 integrated with the central control unit 10 to control the other components of the precious stone testing apparatus. The thermal conductive tube 301 is heated by the PTC heating device 92 and configured as a probe for heat transfer to the stone to be tested S to apply precise temperature control. The PTC heating device 92 is a Positive Temperature Coefficient (PTC) heater, which increases resistance as the temperature rises, providing self-regulating heating, so as to maintain a stable temperature.

When the PTC heating device 92 receives control signals from the central control unit 10 to adjust the heating level as needed. When the stone to be tested S is placed in contact with or near the thermal conductive tube, the thermocouple 3 on the thermal conductive tube 301 functions as a temperature sensor that detects and monitors a temperature of the thermal conductive tube 301 while keeping the temperature within a set range at all times, so as to ensure that the stone to be tested S is heated to a specific temperature required for testing.

The PTC (Positive Temperature Coefficient) heating device 92 is configured for generating the heat required to warm the stone to be tested S. The relay device 93 acts as a switch to control the flow of electrical power to the PTC heating device 92 based on the input from the central control unit 10 and the temperature sensor, thermocouple 52, of the thermal conductive tube 301.

When the central control unit 10 determines to heat the stone to be tested S (based on the temperature data from the thermal conductive tube 301), a voltage is applied across connections L1 and L2 to energize a relay coil of the relay device 93.

Energizing the relay coil causes the relay device 93 to selectively close its internal contacts, specifically between connections L11 and L12 or between connections L21 and L22. The connections L11 and L12 are the relay's first set of contacts. When the relay device 93 is energized (relay coil is activated), these contacts close, allowing current to flow from the power source through the PTC heating device 92. This action turns on the PTC heating device 92, causing it to generate heat that is transferred to the stone to be tested S via the thermal conductive tube 301.

The connections L21 and L22 might be used for an additional control function, such as providing feedback to the central control unit 10 or controlling another circuit element related to the heating or temperature monitoring process.

When the central control unit 10 determines that the stone to be tested S needs to be heated to reach the optimal testing temperature, it energizes the relay device 93 by applying power to connections L1 and L2. This action closes the contacts between connections L11 and L12. With connections L11 and L12 closed, power is supplied to the PTC heating device 92. The PTC heating device 92 begins to warm up, gradually heating the stone to be tested S through the thermal conductive tube 301.

It is worth mentioning that, as the PTC heating device 92 operates, its self-regulating nature prevents it from overheating the testing precious stone. The thermocouple 53 on the thermal conductive tube 301 is configured to continuously send temperature data to the central control unit 10. Once the testing precious stone reaches the desired temperature, the central control unit 10 deactivates the relay device 93 by cutting off the voltage to connections L1 and L2. This opens the contacts between connections L11 and L12, cutting off power to the PTC heating device 92. If connections L21 and L22 are controlling another part of the circuit, they would also open, potentially stopping another related operation.

In other words, the connections L1 and L2 control the relay device 93, determining whether the relay device 93 is engaged or disengaged. The contacts L11 and L12 control the power to the PTC heating device 92, turning it on when the relay device 93 is engaged. The connections L21 and L22 might control an additional function or provide feedback in the circuit, depending on the design. The relay device 93 ensures that the testing precious stone is heated precisely to the required temperature and that the heating system operates safely and efficiently.

Figure 8:
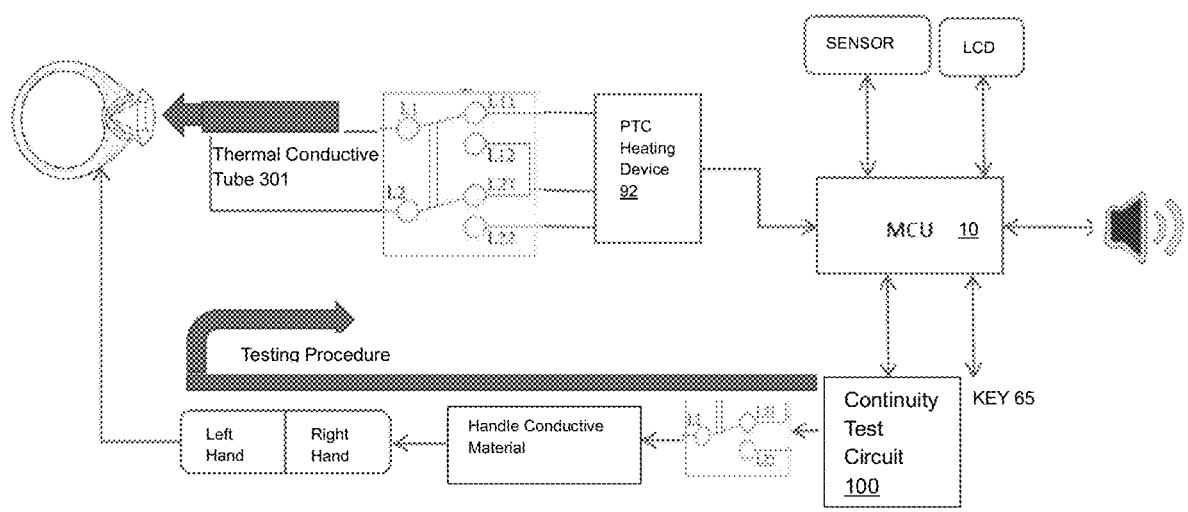
FIG. 8 is a block diagram illustrating a continuous metal detection and testing of the precious stone testing apparatus according to the above preferred embodiment of the present invention.

FIG. 8 is a block diagram illustrating a system for metal detection and testing which is integrated with a continuity test.

The thermal conductive tube 301 is configured as a probe for detecting metal presence and testing continuity in the stone to be tested S, that may be used to direct or apply a signal for testing purposes.

The thermal conductive tube 301 is configured with the PTC heating device 92 and the relay device 93 for temperature management as the heating system 90 as illustrated in FIG. 7. However, the system as illustrated in FIG. 8 further comprises a continuity test circuit 100 that provides a function to maintain optimal conditions for metal detection or testing.

The sensor is the metallic detection device 80 configured for detecting metal presence or continuity and providing feedback to the central control unit 10 for processing and decision-making.

The continuity test circuit 100 is configured to check the continuity of the electrical connectivity of a metallic conductive material of a conductive handle 201 of the housing 2, ensuring electrical connectivity, which interfaces with the central control unit 10 that interprets the test data and provides the test results correspondingly. The continuity test circuit 100 is designed for efficient metal detection and continuity testing, integrating the metallic detection device 80 and user interfaces for streamlined operation.

Figure 9:
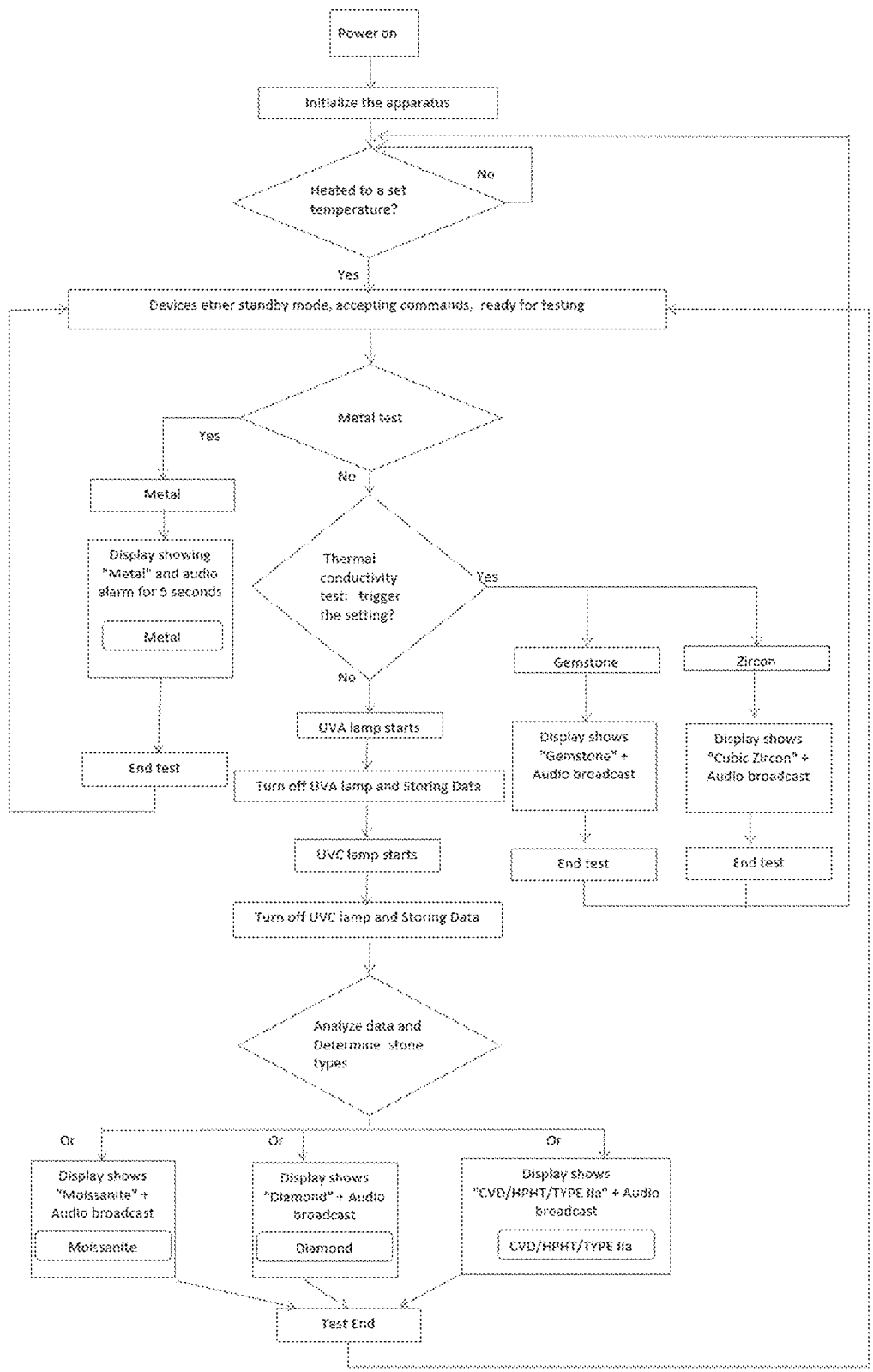
FIG. 9 is a flow chart diagram illustrating the precious stone testing method of the precious stone testing apparatus according to the above preferred embodiment of the present invention.

Referring to FIG. 9, a precious stone testing method of the precious stone testing apparatus as disclosed above is illustrated, comprising steps of:

(a) initializing the precious stone testing apparatus;

(b) determining whether the devices 80, 90 being heated to a set temperature, if yes, the precious stone testing apparatus entering a standby mode, accepting commands and ready for testing, if no, continuing to heat the devices 80, 90;

(c) conducting a metal test by the metallic detection device 80 to determine whether the stone being tested is gemstone, such as the setting around the perimeter of the stone being tested S, if yes, displaying metal test result through the display device 40 and/or providing audio alarm for a predetermined period of time through the audio device 70, if no, go to the next step (d);

(d) conducting a thermal conductivity test by the heating system 90 to determine whether the stone being tested S is gemstone, synthetic gemstone such as cubic zirconia (CZ zircon), if yes, displaying gemstone, synthetic gemstone such as cubic zirconia (CZ zircon) test result through the display device 40 and/or providing audio alarm through the audio device 70, if no, go to the next step (e);

(e) starting the UVA LED lamp 21 and the UVC LED lamp 22 and conducting a UVA test and a UVC test correspondingly to the stone being tested S to determine whether the stone being tested S natural diamond, moissanite or CVD/HPHT/TYPE IIa; and (f) analyzing tested data obtained in the UVA test and the UVC test to determine whether the stone being tested S is natural diamond, moissanite or CVD/HPHT/TYPE IIa and displaying the natural diamond, moissanite or CVD/HPHT/TYPE IIa test result through the display device 40 and/or providing audio broadcast through the audio device 70.

In view of above, according to the preferred embodiment, the operation of the precious stone testing apparatus of the present invention is as simply as placing the testing end of the quartz light guide column 31 of the tester probe unit 3 close to the stone to be tested S, such as near the stone to be tested S or contacting the testing end of the quartz light guide column 31 with the stone to be tested S, while the UVA LED light generated from the UVA LED lamp 21 and the UVC LED light generated from the UVC LED lamp 22 are directed and focused to emit through the quartz light guide column 31 onto the stone being texted, the thermal conductive tube 301, encircling the quartz light guide column 31, applies heat generated from the heating device 92 to the of the stone being tested S at the same time, and that the execution of the testing steps (a) to (f) produces an immediate test result to determine whether the stone being tested S is gemstone, synthetic gemstone such as cubic zirconia (CZ zircon), moissanite, natural diamond, or lab grown diamond (CVD/HPHT/TYPE IIa). In other words, the testing of the precious stone with the precious stone testing apparatus is an all-in-one tester with innovative configuration to avoid deterioration and destruction of the long-wave and short-wave UV lamps 21, 22 to ensure a normal operation of the precious stone testing apparatus all the time.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A precious stone testing apparatus, comprising:

a housing; and a testing circuit, housed in said housing, comprising:

a power source supplying electric power to said testing circuit;

an optical system which comprises at least one UVA/UVC optical sensor and a quartz light guide column having at least one portion extended out of said housing;

a UVA/UVC LED unit comprising a UVA/UVC module which comprises a substrate, a UVA LED chip, a UVC LED chip and a partition member, wherein said substrate is electrically connected to said constant drive via an electrical wiring, wherein said UVA LED chip and said UVC LED chip are arranged in a side by side manner to face said optical system so as to ensure a UVA LED light, in a wavelength range of 320 nm to 400 nm, emitted from said UVA LED chip and a UVC LED light, in a wavelength range of 200 nm to 280 nm, emitted from said UVC LED chip being directed and focused to a stone being tested, and that reflections of the UVA LED light and the UVC LED light after penetrating the stone being tested are guided and focused by the quartz light guide column back to the at least one UVA/UVC optical sensor, wherein said partition member is made of a UVC blocking material and arranged between said UVA LED chip and said UVC LED chip, such that said UVC LED light emitted from said UVC LED chip is blocked by said partition member from irradiating said UVA LED chip of said UVA LED lamp;

a heating system; and a thermal conductive tube, made of thermal conductive material and configured to be heated by said heating system, having at least one portion extended out of said housing in such a manner that said quartz light guide column is arranged and extended in said thermal conductive tube to form a tester probe unit, so that by placing a testing end of said quartz light guide column close to the stone being tested, while said UVA LED light emitted from said UVA LED lamp and said UVC LED light emitted from said UVC LED lamp are directed and focused onto the stone being tested through said quartz light guide column, said thermal conductive tube, encircling said quartz light guide column, applies heat generated from said heating system to the stone being tested at the same time; and a central control unit, which is electrically connected with said power source, said optical system, said UVA/UVC LED unit, said heating system, and said thermal conductive tube and configured to coordinate said UVA/UVA LED unit and said heating system for managing inputs, outputs and operations of said precious stone testing apparatus and providing test results.

2. The precious stone testing apparatus, as recited in claim 1, wherein said substrate has a UVA socket and a UVC socket which are indented in an emitting side thereof and configured to face said optical system, wherein said UVA LED chip is arranged in said UVA socket to form a UVA LED lamp and said UVC LED chip is arranged in said UVC socket to form a UVC LED lamp.

3. The precious stone testing apparatus, as recited in claim 2, wherein said partition member is a partition wall isolating said UVA socket and said UVC socket in said emitting side of said substrate.

4. The precious stone testing apparatus, as recited in claim 1, wherein said UVA LED chip is arranged close to one side of said partition member and said UVC LED chip is arranged close to another side of said partition member.

5. The precious stone testing apparatus, as recited in claim 3, wherein said UVA LED chip is arranged close to one side of said partition member and said UVC LED chip is arranged close to another side of said partition member.

6. The precious stone testing apparatus, as recited in claim 1, wherein said UVC LED chip is larger than said UVA LED chip and said UVC socket is larger than said UVA socket in size.

7. The precious stone testing apparatus, as recited in claim 3, wherein said UVC LED chip is larger than said UVA LED chip and said UVC socket is larger than said UVA socket in size.

8. The precious stone testing apparatus, as recited in claim 5, wherein said UVC LED chip is larger than said UVA LED chip and said UVC socket is larger than said UVA socket in size.

9. The precious stone testing apparatus, as recited in claim 1, wherein said heating system comprises a heating device and a heating drive, connected with said central control unit, wherein said heating device is configured to heat said thermal conductive tube and controlled by said central control unit through said heating drive.

10. The precious stone testing apparatus, as recited in claim 9, wherein said heating device is a PTC (positive temperature coefficient) heating device and said optical system further comprises a UVA/UVC optical sensor configured to monitor light intensity and detect reflections of said UVA LED light and said UVC LED light, one or more operational amplifiers configured to be used in said UVA/UVC optical sensor for signal amplification and conditioning.

11. The precious stone testing apparatus, as recited in claim 10, wherein a relay device is arranged between said PTC heating device and said thermal conductive tube, providing electrically operated switches via L1, L2, L11, L12, L21, and L22 connections for controlling a flow of electrical current in said testing circuit, wherein said L1 and L2 connections are main power input lines to a relay coil of said relay device, such that when said relay device is energized by applying voltage across said L1 connection and said L2 connection, contacts between corresponding pairs of said L11, L12, L21, and L22 connections are closed, allowing current to pass through said L11, L12, L21, and L22 connections.

12. The precious stone testing apparatus, as recited in claim 11, wherein said L11 connection and said L12 connection are a pair of contacts within said relay device and arranged in such a manner that when said relay device is energized, said L11 connection and said L12 connection would close, allowing current to flow therebetween, such that a power supply to said PTC heating device is controlled while a turning on or off depending on whether said relay device is engaged, wherein said L11 connection and said L12 connection are connected to said thermal conductive tube, acting as a sensor to provide a temperature feedback to said central control unit, wherein said L21 connection and said L22 connection are another pair of contacts within said relay device and arranged in such a manner that when said relay device is energized, said L21 connection and said L22 connection close, allowing current to flow therebetween, such that a part of power to said control unit and said PTC heating device is controlled, wherein said L21 connection and said L22 connection are linked to said thermal conductive tube so as for controlling an operation of said testing circuit based on said temperature feedback from said thermal conductive tube, so that said thermal conductive tube is also configured as a temperature sensor that monitors a temperature of the thermal conductive tube while keeping the temperature within a set range at all times and sends detected data to said central control unit.

13. The precious stone testing apparatus, as recited in claim 12, wherein said central control unit processes said temperature data from said thermal conductive tube and determines whether to energize said L1 connection and said L2 connection of said relay device, such that when a temperature is below a certain threshold, said central control unit energizes said relay device, closing said contacts between one of a pair of said L11 connection and said L12 connection and a pair of said L21 connection and said L22 connection, thereby powering said PTC heating device, and that when said temperature reaches said predetermined threshold, said central control unit de-energizes said relay device, opening said contacts between said one of pair of said L11 connection and said L12 connection and said pair of said L21 connection and said L22 connection, cutting off said power to said PTC heating device.

14. The precious stone testing apparatus, as recited in claim 8, wherein said heating system comprises a heating device and a heating drive, connected with said central control unit, wherein said heating device is configured to heat said thermal conductive tube and controlled by said central control unit through said heating drive.

15. The precious stone testing apparatus, as recited in claim 14, wherein said heating device is a PTC (positive temperature coefficient) heating device and said optical system further comprises a UVA/UVC optical sensor configured to monitor light intensity and detect reflections of the UVA LED light and the UVC LED light, one or more operational amplifiers configured to be used in the UVA/UVC optical sensor for signal amplification and conditioning.

16. The precious stone testing apparatus, as recited in claim 15, wherein a relay device is arranged between said PTC heating device and said thermal conductive tube, providing electrically operated switches via L1, L2, L11, L12, L21, and L22 connections for controlling a flow of electrical current in said testing circuit, wherein said L1 and L2 connections are main power input lines to a relay coil of said relay device, such that when said relay device is energized by applying voltage across said L1 connection and said L2 connection, contacts between corresponding pairs of said L11, L12, L21, and L22 connections are closed, allowing current to pass through said L11, L12, L21, and L22 connections.

17. The precious stone testing apparatus, as recited in claim 16, wherein said L11 connection and said L12 connection are a pair of contacts within said relay device and arranged in such a manner that when said relay device is energized, said L11 connection and said L12 connection would close, allowing current to flow therebetween, such that a power supply to said PTC heating device is controlled while a turning on or off depending on whether said relay device is engaged, wherein said L11 connection and said L12 connection are connected to said thermal conductive tube, acting as a sensor to provide a temperature feedback to said central control unit, wherein said L21 connection and said L22 connection are another pair of contacts within said relay device and arranged in such a manner that when said relay device is energized, said L21 connection and said L22 connection close, allowing current to flow therebetween, such that a part of power to said control unit and said PTC heating device is controlled, wherein said L21 connection and said L22 connection are linked to said thermal conductive tube so as for controlling an operation of said testing circuit based on said temperature feedback from said thermal conductive tube, so that said thermal conductive tube is also configured as a temperature sensor that monitors a temperature of the thermal conductive tube while keeping the temperature within a set range at all times and sends detected data to said central control unit, wherein said central control unit processes said temperature data from said thermal conductive tube and determines whether to energize said L1 connection and said L2 connection of said relay device, such that when a temperature is below a certain threshold, said central control unit energizes said relay device, closing said contacts between one of a pair of said L11 connection and said L12 connection and a pair of said L21 connection and said L22 connection, thereby powering said PTC heating device, and that when said temperature reaches said predetermined threshold, said central control unit de-energizes said relay device, opening said contacts between said one of pair of said L11 connection and said L12 connection and said pair of said L21 connection and said L22 connection, cutting off said power to said PTC heating device.

18. The precious stone testing apparatus, as recited in claim 1, wherein said testing circuit further comprises a continuity test circuit which comprises a metallic detection device configured for detecting metal presence or continuity and providing a feedback to said central control unit, wherein said continuity test circuit is configured to a the continuity of an electrical connectivity of a metallic conductive material of a conductive handle of said housing, ensuring electrical connectivity, which interfaces with said central control unit that interprets test results.

19. The precious stone testing apparatus, as recited in claim 13, wherein said testing circuit further comprises a continuity test circuit which comprises a metallic detection device configured for detecting metal presence or continuity and providing a feedback to said central control unit, wherein said continuity test circuit is configured to a the continuity of an electrical connectivity of a metallic conductive material of a conductive handle of said housing, ensuring electrical connectivity, which interfaces with said central control unit that interprets test results.

20. The precious stone testing apparatus, as recited in claim 17, wherein said testing circuit further comprises a continuity test circuit which comprises a metallic detection device configured for detecting metal presence or continuity and providing a feedback to said central control unit, wherein said continuity test circuit is configured to a the continuity of an electrical connectivity of a metallic conductive material of a conductive handle of said housing, ensuring electrical connectivity, which interfaces with said central control unit that interprets test results.

* * * * *